(12) United States Patent
Mock

(10) Patent No.: US 8,257,244 B2
(45) Date of Patent: Sep. 4, 2012

(54) INTRAUTERINE DEVICE, METHOD OF MAKING SUCH A DEVICE AND METHOD FOR PUTTING ACTIVE ELEMENTS WITHIN THE UTERINE CAVITY

(75) Inventor: Pascal Mock, Geneva (CH)

(73) Assignee: Anecova SA, Geneva (CH)

( * ) Notice: Subject to any disclaimer, the term of this patent is extended or adjusted under 35 U.S.C. 154(b) by 1258 days.

(21) Appl. No.: 10/485,611

(22) PCT Filed: Jul. 22, 2002

(86) PCT No.: PCT/IB02/03363
§ 371 (c)(1),
(2), (4) Date: Aug. 18, 2004

(87) PCT Pub. No.: WO03/011200
PCT Pub. Date: Feb. 13, 2003

(65) Prior Publication Data
US 2004/0261799 A1    Dec. 30, 2004

Related U.S. Application Data

(60) Provisional application No. 60/309,274, filed on Aug. 1, 2001.

(51) Int. Cl.
*A61B 17/43* (2006.01)
(52) U.S. Cl. .................................................. 600/33
(58) Field of Classification Search .......... 600/33–35; 128/830, 897, 899; 604/890.1, 906
See application file for complete search history.

(56) References Cited

U.S. PATENT DOCUMENTS

| | | | |
|---|---|---|---|
| 3,659,596 A | 5/1972 | Robinson | |
| 3,911,911 A * | 10/1975 | Scommegna | 128/833 |
| 3,971,367 A * | 7/1976 | Zaffaroni | 128/833 |
| 4,552,557 A * | 11/1985 | Rangaswamy | 604/103.1 |
| 5,084,004 A | 1/1992 | Ranoux | |
| 5,158,881 A | 10/1992 | Aebischer et al. | |
| 5,626,148 A | 5/1997 | Lehtinen | |
| 6,050,935 A * | 4/2000 | Ranoux et al. | 600/33 |
| 6,054,142 A | 4/2000 | Li et al. | |
| 6,610,005 B1 * | 8/2003 | Tao | 600/34 |
| 2002/0076399 A1* | 6/2002 | Braun | 424/93.21 |
| 2003/0176763 A1* | 9/2003 | Eckstein | 600/35 |

FOREIGN PATENT DOCUMENTS

| | | |
|---|---|---|
| CN | 94229787.3 | 10/1995 |
| GB | 2276322 A * | 9/1994 |
| KR | 1019990049972 | 6/2001 |
| WO | WO 9639098 | 12/1996 |

OTHER PUBLICATIONS

Li, Rebecca H.; *Materials for immunoisolated cell transplantation*; Advanced Drug Delivery Reviews 33 (1998) 87-109; © 1998 Elsevier Science B.V.

Aebischer, et al.: "*Intrathecal delivery of CNTF using encapsulated genetically modified xenogeneic cells in amyotrophic lateral sclerois patients*", Nature Medicine, vol. 2, No. 6, Jun. 1996; Nature Publishing Group.

* cited by examiner

*Primary Examiner* — Charles A Marmor, II
*Assistant Examiner* — Christine Hopkins
(74) *Attorney, Agent, or Firm* — Hunton & Williams, LLP

(57) ABSTRACT

A retrievable intrauterine device for placing within a uterine cavity one or more encapsulated elements capable of having interactions with uterine fluid comprising an intrauterine device loaded with the encapsulated elements.

15 Claims, 1 Drawing Sheet

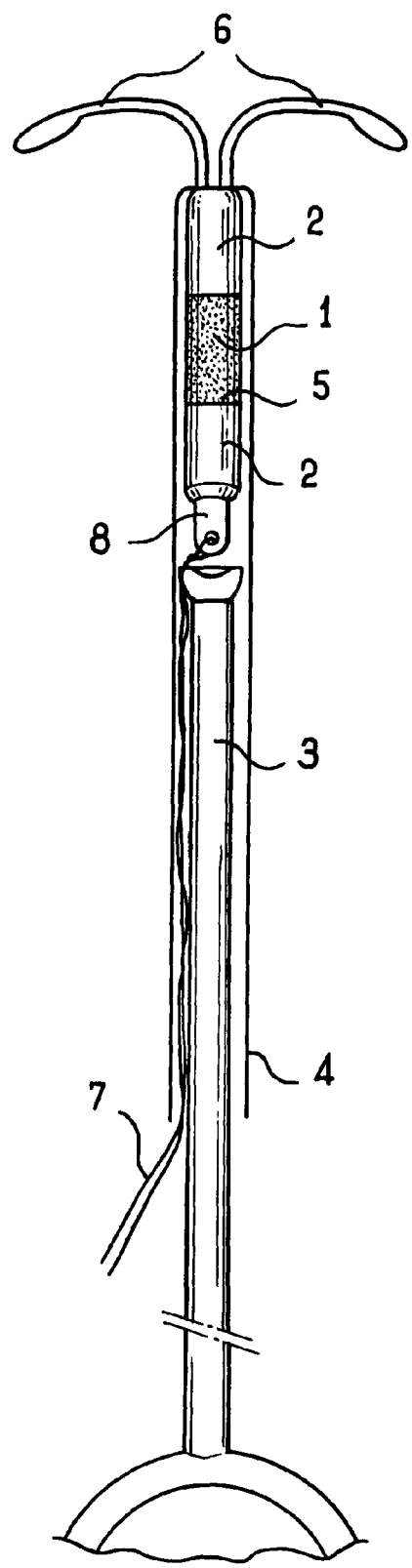

INTRAUTERINE DEVICE, METHOD OF MAKING SUCH A DEVICE AND METHOD FOR PUTTING ACTIVE ELEMENTS WITHIN THE UTERINE CAVITY

CROSS REFERENCE TO RELATED APPLICATIONS

This application is the national phase of PCT/IB02/03363, filed Jul. 22, 2002. Priority is claimed to U.S. Provisional Application No. 60/309,274 filed Aug. 1, 2001.

BACKGROUND OF THE INVENTION

The present invention relates generally to intrauterine devices and to method for placing elements into the uterine cavity notably for therapeutic purposes. The uterine cavity is an anatomical location which the direct access is not easy and until now, the intrauterine devices are only used in the art of contraceptive methods. However, the uterine cavity may be used for several other purposes with an appropriate intrauterine device, notably for treating directly the uterine wall (endometrium and/or myometrium), for temporary in vivo embryo/egg incubation and as an appropriate administration way to reach the general blood system. The present invention provides with means in this connection.

SUMMARY OF THE INVENTION

The present invention relates to a retrievable intrauterine (uterine cavity or Fallopian tube) device notably for implantation of gametes or embryos into the uterus (or tube) allowing to perform in vivo and in utero (or intraFallopian tube) fertilization and/or preimplantatory development in assisted reproductive technology (ART).

The invention also relates to a similar intrauterine device for implantation of genetically modified cell lines by genes transfection into the uterus in order to deliver molecules near the endometrium without systemic effect and permitting to modify and prepare more specifically the endometrium before embryo transfer after ART or natural conception, or in contrary to avoid any pregnancy (contraception) as standard IntraUterine Device (IUD).

The invention also relates to a similar intrauterine device allowing the delivery of various active elements within the uterine cavity.

In particular, said active elements can be both gametes/embryos and genetically modified cell lines by genes transfection for bioactive factors secretion in order to improve the uterine environment for in vivo incubated gametes/embryos (embryos possibly resulting from cloning or any other technique).

The present invention can be applied to any mammalian species.

According to a first aspect, the invention concerns reproductive medecine in particular the in vitro fertilization (IVF) in assisted reproductive technology and drug delivery from the uterus using an intrauterine device associated to cell encapsulation technology.

Since the introduction in 1978, IVF has become the preferred procedure for addressing most causes of infertility in humans. As a part of the IVF process, the reproductive cells (oocytes and spermatozoa) and the resulting fertilized oocytes (zygotes, embryos) are treated according to specified procedures using in vitro culture media adapted to each specific step in the procedure.

A standard in-vitro fertilization (IVF) comprises the following steps:

Maturation (Oocyte recruitment)

To ensure maturation of more than one oocyte, the women are treated with hormones prior to the actual fertilization procedure. Usually the woman is treated for 14-21 days with a element (GnRH agonist) which will disrupt then normal hormonal control signals between the brain (hypothalamus and pituitary) and the ovary. Thereafter relatively large doses of FSH (Follicle Stimulating Hormone) are administered for 10-20 days depending on ovarian response. FSH will stimulate to maturation of many follicles each containing an oocyte.

When the oocytes are ready for ovulation, human Chorionic Gonadotrophin (hCG) is administered to finalize oocyte maturation.

Aspiration of oocytes

After maturation in vivo, the oocytes are collected from the woman's ovaries using ultrasound guided follicular puncture.

Fertilization and embryo culture

In vitro fertilization is obtained by adding spermatozoa to the oocytes (In vitro fertilization <<IVF>>) or by microinjecting one spermatozoon into each mature oocyte (Intracytoplasmatic sperm injection-ICSI). The fertilized oocytes are cultivated in IVF media outside the genital tract for two to five days.

Embryo transfer

After two to five days of embryo in vitro culture a few embryos are selected and transferred into the woman's uterus using a thin catheter.

The ultimate goal of in vitro fertilization and embryo culture is to provide high quality embryos that are capable of continuing normal development and results in live births.

In vitro culture for preimplantatory embryo development Despite nearly 20 years of treating patients with IVF and more recently intracytoplasmic sperm injection (ICSI), implantation rates per embryo transferred remain low, on average about 20%.

Most IVF centers around the world perform the embryo transfer at day 2 or 3 which means 3 or 2 days before the physiological implantation time. Recent development in the field of embryo physiology and metabolism have led to the formation of new sequential serum-free culture media designed to simulate the dynamic environment as the embryo travel along the reproductive tract (Gardner et al., 1996). Sequential culture media systems (G1.2/G2.2) have the highest rate of blastocyst formation which remains low at 50% (Gardner et al., 1998).

The rationale for culturing embryos to the blastocyst stage is that it allows selection for transfer of embryos with proven developmental capacity. Furthermore, the transfer of a blastocyst into the uterus is physiologically closer to the in vivo situation than transferring an early cleaving embryo that would normally be present in the Fallopian tube and has less risk to be expulsed from the uterus because of a reduced time before embryo implantation.

Most recent papers have shown the beneficial effect of in vitro coculture of the zygote with human endometrial epithelial (Simon et al., 1999) and/or stromal (Barmat et al., 1998) cells on the number of blastomeres per preembryo, the rate of development to the morula-blastocyst stage, the rate of spontaneous hatching and the percentage of cytoplasmic fragments, and implantation rate as recently described by Spandorfer et al., 2002.

In the report of the year 1994 of assisted reproductive technology activities in the United States and Canada, gamete intrafallopian transfer (GEM and zygote intrafallopian transfer (ZIFT) have the higher rate of clinical pregnancy compared to in vitro fertilization. More recently, Levran et al., in 2002 demonstrate that zygote intrafallopian tube transfer improve the outcome in repeated implantation failure compared to a tranfer of blastocysts after standard IVF.

These findings would suggest that the presence of zygote into the upper genital tract may be important for the embryo development profiting of all known and unknown growth factors present in the uterine fluid and its potentiality to invade the endometrium during the implantation process.

Furthermore, in bovine studies have recently demonstrated that in vivo produced embryos were less altered compared to in vitro ones, with more intercellular communication devices (Boni et al., 1999) and more mature mitochondria in particular (Crosier et al., 2000).

All the above mentioned studies confirm that in vitro embryo preimplantatory development is far to be optimal instead of all efforts to optimize culture media by mimic uterine fluid characteristics.

The present invention provides with a novel method in ART using the cell encapsulation technology in order to notably permit to gametes and/or preimplantatory zygotes/embryos in IVF programmes (or cloning for all other mammalian species) to benefit from a temporary natural incubation into the uterus.

Furthermore, a controlled in time of the intrauterine incubation may lead to a better quality of embryo development and consequently to a higher implantation rate, and it may have an economical advantage with a lower cost/benefit to the standard IVF procedure above all if blastocyst transfer is generalized in ART units.

According to a second aspect, the invention relates to the in utero delivery of active elements by the implantation of tissues, cells or cell lines, possibly genetically modified, notably for cellular therapy.

In all mammallian species the success of implantation is related to a perfect crosstalk between a good quality embryo and a receptive endometrium.

In the domain of assisted reproductive technology (ART), clinicians are limited in the control of the complex events of endometrium receptivity by endocrinological treatment by the administration of 17beta estradiol and progesterone to mimic the physiological sequential follicular and luteal phases.

In the basic science literature, most studies are now focusing on the paracrinology of periimplantation between the embryo and the endometrium using in vitro and in vivo models as knock-out mouses lacking the interest molecule. For instance, it has been shown that in integrin beta1-deficient mice (Fassler and Meyer, 1995) and female mice with a null mutation of interleukin-11 receptor alpha chain (Robb et al., 1998) embryos failed to implant.

However, in rodents it is establihed that direct contact between the embryo and the endometrium is not necessary (Shiotani et al., 1993). Whereas embryo implantation rate is remained stable and low since two decade we can say that endocrine manipulation with vaginal progesterone and hCG systemic administration and finally 17beta oestradiol are far to be optimal and quite far to the complexe paracrinology of embryo implantation processes.

The present invention provides a novel concept in ART using the cell encapsulation technology in order to implant cell lines genetically modified secreting a molecule of interest near the endometrium temporary before embryo transfer in IVF programmes.

Such an intrauterine molecule(s) or "drug" delivery, closer to the target tissue permits a better and more selectively preparation of the endometrium and a use of small molecules with short half time or molecules with secondary effects forbidden in systemic administration.

According to a third aspect, the invention relates to an implantable/insertable device to deliver agents capable of preparing the uterus before receiving embryo(s) before implantation into the wall of the uterus or for treating the uterus. With respect to this embodiment, certain or most drugs, nutrients, vitamins, amino acids, fatty acids, peptides, proteins and the like capable of stimulating the uterus specifically with respect to preparation of embryo implantation, or any other therapeutical agent can also be easily delivered by the device of the invention containing polymers or cells releasing these agents. In fact, the retrievable intrauterine device of the invention for drug delivery has specific advantages for women who can not receive drugs normally given by injection or other delivery routes. In addition, delivery of agents through the uterine wall may be an optimal means for treating forms of reproductive system cancers and/or other reproductive diseases, as well as any uterine diseases.

The invention notably provides a cell encapsulation intrauterine device for in vivo and in utero gametes fertilization and/or embryo preimplantatory development with a control of time (from several minutes to 48, 72 h) where the uterus play a role of "natural incubator" before the definitive embryo transfer in IVF programmes.

Thus, the cell encapsulation intrauterine device of the invention is a novel and modified intrauterine device, similar to contraceptive IUD as described in U.S. Pat. No. 3,628,530 by Jerome Schwarz in 1969 and in U.S. Pat. No. 3,516,403 by René Cournut in 1967, which has, according to the present invention, to permit a temporary introduction of gametes or embryos associated or not to other somatic cells (in vivo coculture) into the uterine cavity and its retrieval after a defined time by using a cell encapsulation technology as described in WO 91/00119 by Thomas Mandel et al. in 1989, WO 01/64185 A2 by Newman and Kram in 2000 and in U.S. Pat. No. 5,158,881 by Aebischer et al. in 1990 and U.S. Pat. No. 6,054,142 by Li et al. in 1996.

In fact, the present invention concerns a retrievable intrauterine device for placing within the uterine cavity one or more encapsulated element(s) capable of having interactions with the uterine fluid comprising an intrauterine device loaded with encapsulated elements.

According to the present invention, the term "element(s)" means any organic or inorganic, cellular or molecular, natural or synthetic compound(s) or substance(s).

The term "loaded" encompasses not only the case where the intrauterine device of the invention is the support of said encapsulated element which can be for is example be adsorbed on the surface of said device, but also the case where said elements are contained within the device of the invention. According to a preferred embodiment, the retrievable intrauterine device of the invention is provided with at least one housing in which said encapsulated element(s) is/are loaded. Different elements may be mixed in the same housing or placed in separate housings.

The expression "capable of having interactions with the uterine fluid" encompasses not only the case where said elements are delivered by the device of the invention in the uterine fluid in order to produce an effect on the wall (endometrium and/or myometrium) of the uterine cavity (first case), but also the case where said elements are staying within the device and have known or unknown exchanges or interactions with the uterine fluid and/or with the uterine wall (endometrium and/or myometrium) (second case).

According to a first aspect of the "first case", said elements may be not only agent(s) capable of treating the uterus but also agent(s) capable of treating any pathology. In fact, agent(s) capable of treating the uterus will be delivered from the device of the invention into the uterine fluid and will have an effect directly on the wall of the uterine cavity. This kind of agent is selected from the group comprising agent(s) capable of preparing the uterine wall for optimal embryo implantation, agent(s) capable of preparing the uterine wall for optimal egg culture, agent(s) capable of therapeutically treating the uterus and contraceptive agent(s).

The advantage of such a system allows using agents capable of having a direct effect of the target organ in avoiding the systemic way.

Furthermore, according to a second aspect of the "first case", the device of the invention can allow the delivery of agents capable of treating any pathology by the in utero administration. In other words, this kind of agent will be delivered in the uterine fluid, will then enter into contact with the wall of the uterine cavity and will pass through the venous system of the endometrium before passing through the general blood system. In other words, the in utero administration is a possible way of administration of any drug likely to treat any pathology in connection with any organ.

Among the elements likely to be loaded in the retrievable intrauterine device of the invention, one must also cite tissues, cells or cell lines secreting one or more agent(s) (for cellular therapy), somatic cells, stem cells (totipotent cells), recombinant viruses as gene transfer vehicle (for gene therapy), sens or antisens mRNA sequences, male and/or female gametes, fertilized oocyte (two pronuclei cell), unfertilized egg and any combination of the above elements.

The above "second case" concerns fertilized oocyte (two pronuclei cell) and unfertilized egg where the uterus plays the role of a natural incubator allowing the culture of said embryo or egg in a natural medium in lieu of an in vitro medium. In this case, no element loaded in the intrauterine device of the invention is delivered into the uterine fluid and the expression "having interactions with the uterine fluid" encompasses the situation where the embryo or the egg has exchanges or interactions with the environmental medium constituted by the uterine fluid and the uterine wall.

According to a preferred embodiment of the present invention, the at least one agent secreted by tissues, cells or cell lines is selected from the group comprising drugs, hormones, nutrients, peptides, proteins, antibodies, trophic factors, growth factors, lymphokines, cytokines, enzymes, blood coagulation factors, angiogenesis factors, analgesics, neurotransmitters, neuromodulators. In this connection, the present invention encompasses the case where tissues, cells or cell lines secreting agents likely to be loaded in the device of the invention can be genetically modified in order to obtain the secretion of the desired product.

According to another preferred embodiment of the invention, the agent capable of therapeutically treated the uterus is selected from the group comprising anti-inflammatory agents, amino acids, fatty acids, antibodies, trophic factors, growth factors, lymphokines, cytokines, enzymes, proteins, peptides, blood coagulation factors, angiogenesis factors, analgesics, neurotransmitters, neuromodulators, anxiolytics, antidepressants, antibiotics, sens or anti-sens mRNA sequences, recombinant viruses as gene transfer vehicle.

According to another embodiment of the preset invention, the element loaded in the retrievable intrauterine device of the invention is capable of treating cancers, forms of reproductive system cancers, reproductive diseases and uterine diseases such as endometriosis, adenomyosis, bleeding disorders and various infections (non limitative list).

In fact, the device of the invention presents a number of advantages: said device is not likely to cause any trouble to the uterus due to the fact that it is not implanted within the uterine wall, it does not require surgery or anesthesia to be inserted and it can be inserted in a completely ambulatory fashion. Furthermore, elements may be delivered in phase with the natural menstrual cycle and in association with hormone dependent gene expression systems controlling drug delivery from the device. It is also very important to note that, as the percutaneous way of administration, the in utero administration allows to avoid the first hepatic passage of the administered element(s). This causes less toxicity and said element(s) present(s) a better bio availability. Finally, said device can be rapidly retrieved with surgical intervention.

BRIEF DESCRIPTION OF THE DRAWINGS

FIG. 1 illustrates an example of device according to the present invention (with 1: capsule, 2: support zone A-distal part- and support zone B-proximal part, 3: plunger, 4: protective tube, 5: membrane or valve for disclosure, 6: wings, 7: removal, 8: silicone tether).

DETAILED DESCRIPTION OF PREFERRED EMBODIMENTS

As example, the device of the invention comprises:
1. a capsule
non-biodegradable
semi permeable
polymeric material (i.e. polyethersulfone or PES. Source=Akzo Nobel Faser AG, Wuppertal, Germany) hollow fibers such as polyacrylates (including copolymers), polyvinylidienes, polyurethanes pores: has to be adapted for an optimal environment quality with a permeability from small to large molecules present into the uterine fluid
Pore-size: from 0.005 μm=molecular weight cutoff of 150 kDa to 280 kDa
Pore-structure: microporous or any adapted structure
Outer diameter=adapted to the optimal size to go through the cervix into the uterine catheter (i.e. 700 μm)
inner diameter=adapted to the size of egg or embryo (i.e. 500 μm), around 5 times the egg or embryo size (egg size with the corona radiata=200 μm in human), or adapted to the size of the molecules to be delivered,
length adapted to the uterine cavity avoiding endometrial lesions and any deleterious factor by uterine distension and finally its expulsion (i.e. about 1.5 cm)
cylindric shape or any adapted shapes for the uterine cavity taking into account the above-mentionned point.
2. two supports, zones A (distal) and B proximal) as described for IUD in U.S. Pat. No. 3,628,530 by Schwarz with the following modification:
distal part (A) closed by acrylate-based glue, Luxtrack LCM 23 (Ablestik, USA) or any other system as cap, proximal part (B), hollow and openable with a one sens direction (on the inside) valve.
zone A support comprises two wings or any other devices (it can comprises asymetrical wings in a similar material than the support covered by a thin hydrophilic material which becomes thicker at fluid contact) in a similar material or others than the support permitting a stable position of the device into the uterus.

zone B support comprises a silicone tether to attach the removing thread in order to retrieve the device 3. plunger
4. an operating handle being coupled with the plunger
5. a removing fiber for removing the intrauterine encapsulating device
6. an attachement device for attaching the removing fiber ensuring immovable position of the intrauterine encapsulating device with respect to the plunger
7. a protective tube encompassing the plunger as described by Lehtinen Matti et al. in 1994 (patent number CZ 286 820), but with a plunger permitting the loading of gametes, embryos, drugs or any other element with a standard pipette by the IVF biologist.

The present cell encapsulation intrauterine device may take any shape which will accommodate gametes and/or embryos or any other above mentioned element to be encapsulated using an adapted micropipette for loading. A preferable implantable embryo culture device is a tubular, selectively permeable membrane with an adapted pore size in order to permit adequate nutrients transfer to the embryo such as O2, proteins, growth factors and other known and unknown factors released from the endometrium, having one end through which gametes or embryos are loaded into cell compartment. The controlateral end may then be permanently occluded with caps or alternatively with an epoxy glue or sutures of a biocompatible and non resorbable material like polypropylene.

Concerning the structure of the retrievable intrauterine device according to the present invention, a retrievable hollow fiber device with internal diameter, dimensions ranging from 100-10,000 microns and having a suitable means for attachment of the device to uterine cavity (wall) is ideal as an egg/embryo chamber for inter uterine incubation. The current device design employed in connection with the present invention is a Polyethersulfone membrane with MW cutoff of approximately 240,000 daltons, wall diameter of 100 microns and inner diameter of 472 microns. Wall thickness can range from 50-500 microns depending on the composition, porosity, hydraulic permeability, pore size and strength of the encapsulating material. Molecular weight cutoffs can vary from 50,000 to >1 million molecular weight. Furthermore, the encapsulating material can be composed of any biocompatible material including Polyethersulfone, Pan-PVC or expanded PTFE and formulated with laminated or single membrane structures. The encapsulating device may or may not contain a matrix or internal lining material. The length can range from 0.5 cm-5 cm or what ever will fit comfortably within the uterus. As indicated above, one of the most important considerations for this device are that it be capable of holding an embryo without damage for incubation directly in the uterus to be fully retrievable. In addition, the device has been designed with little or no tissue reaction, with smooth surfaces such that it will be implantable/insertable and retrievable without inducing inflammatory or fibrotic reactions and or inappropriate uterine wall tissue damage or scarring. Finally, the device has been designed such that it has a means of remaining within the uterus (i.e. small suture thread glued into the tip of the device for attachment inside or outside the uterus) and that can be easily retrieved (attached suture thread) at any time after uterine implantation. Devices similar in composition to those used currently by Modex Therapeutics (PES 5, PES 1, PES 10/10) hollow fiber device and used in the past by Cytotherapeutics (Pan-PVC) are ideal for such applications although any device, which meets this general description will be appropriate for the contemplated uses.

The device of the invention can be surgically implanted passing through the cervix as a standard IUD for contraception into the uterus and removed after a defined time of incubation.

However, the present invention may use as implantation site the Fallopian tube permitted by a modification of the present cell encapsulation intrauterine device for instance without the distal part with the two wings. This implantation is more difficult in access and need to use a surgical procedure as coelioscopy with general anesthesia or culdoscopy with local anaesthesia. Such in vivo intra Fallopian embryo culture is similar to GIFT or ZIFT except the fact that using the cell encapsulation device of the invention the incubation time is under control and an unlimited number of embryos can be loaded which were retrieved and selected for transfer after a simple flushing procedure.

Thus, zygotes or embryos at different stages (day 2 to 5) can be loaded with a standard micropipette into the capsule of the cell encapsulation intrauterine device of the invention after standard IVF with or without ICSI.

The invention also relates to a method of preparing a retrievable intrauterine device for placing one or more encapsulated elements capable of having interactions with the uterine fluid comprising the steps of:
   providing said element under the appropriate form to be encapsulated,
   providing a retrievable intrauterine device suitable for receiving encapsulated element(s),
   loading said device with said element(s).

The invention also relates to a method for placing one or more encapsulated elements capable of having interaction with the uterine fluid comprising the steps of:
   providing a retrievable intrauterine device,
   implanting said device within the uterus cavity for a determined duration.

According to a preferred embodiment of the invention, the above method is carried out in the uterine cavity of a mammal preferably selected from the group comprising bovine, ovine, porcine and humans.

More particularly, the present invention may be carried out according to the following process:

A. In Vivo Fertilization

Injection of prepared sperm and retrieval oocytes in the encapsulating device for implanting into the uterus. After a defined and controlled incubation time (2 hours par exemple) of in vivo and in utero culture, encapsulated sperm and oocytes are retrieved and zygotes and/or non fertilized oocytes are collected-after a simple flushing procedure. Selection of zygotes for cryopreservation or in vitro culture of the remaining embryos to be transferred at day 3.

B. In Vivo Preimplantatory Embryo Development

Conventional in vitro fertilization of prepared sperm and retrieved oocytes. Injection of several embryos at different stage of development (i.e 6-8 cells) in the cell encapsulation device permitting the implantation into the uterine cavity during a controlled time (i.e 48 hours). After removal from the uterus the encapsulating system device embryos at the blastocyst stage are flushed from the device and transferred into the uterine cavity using a conventional transfer catheter or delayed in a further cycle after freezing.

C. In Vivo Embryo Assisted Hatching

Recently, it has been demonstrated that the process of blastocyst hatching as well studied and described in in vitro programmes has been erroneously accepted in rodents as representing a natural event (Gonzales et al., 2001). Indeed, it seems in hamster species that the uterine contribution in vivo to blastocyst escape from the zona pellucida, consisting of proteinases secreted from the uterus, is the primary mechanism for zona loss in utero, whereas the in vitro lytic activity is secondary to the invasive behavior of trophectoderm.

Taking into account such surprising results, the present invention using the intrauterine cell encapsulation device of the invention to incubate temporary embryos can be used to perform a novel method for assisted hatching: the in vivo embryo assisted hatching.

On this basis, in vivo and in utero culture of the gametes and/or preimplantatory embryos with a time control using the cell encapsulation device of the invention will permit a real dialogue at the embryo-maternal interface with a paracrine action of several known but also unknown factors from endometrium (or from the tube in case of intrafallopian implantation) and embryos important for the optimal embryo development which will lead to a better success of implantation process in ART programmes.

Other scientists have described gametes or embryos encapsulation (Loi et al., 1992; Nebel et al., 1993). However, they all used biodegradable materials (sodium alginate) and have as objectives to eliminate several problems associated with the procedure of embryo transfer (trauma) and to improve embryo protection before implantation and to protect the free zona pellucida of the embryo (Cosby et al., 1990; Adaniya et al., 1993).

To the best of the knowledge of the inventor, the novel concept described in the present invention permitting a natural incubation of gametes and/or embryo by using the cell encapsulation device of the invention has never been published or proposed by scientists.

The invention also provides with a method using a cell encapsulation device with genetically cell lines by genes transfection as described in U.S. Pat. No. 4,686,098 by Kopchick et al. in 1984 and No 4,892,538 by Aebischer et al. in 1987 modified in order to be implanted into the uterine cavity which has never been published by scientists before the present invention.

This novel device as mentioned above permits a novel method to deliver from the uterine cavity molecules near the endometrium without systemic effect and permit to modify and prepare more specifically the endometrium before embryo transfer after in vitro fertilization in ART or natural conception, or in contrary to avoid any pregnancy (anti-implantatory, anti-fertilization) as standard IUD.

This novel concept of bioactive factors delivery into the uterine cavity may lead to a better understanding of the specific paracrine effect on the endometrium tissue and may permit in the near future the development of a novel and complementary cellular therapy approach to modulate and prepare the endometrium for embryo implantation in ART.

Example 1

In Vivo and In Utero Embryos Culture in a Mouse Model

The purpose of this experiment was to evaluate the ability to perform in vivo and in utero preimplantatory embryo development using a modified semi-permeable hollow fiber as a capsule in a mouse model.

Zygotes were obtained using a standard ovarian stimulation protocol in 4- to 5-week old prepubertal females using 5 IU PMSG, which corresponds to day 1 of the procedure (Folligon, Veterinaria) and 5 IU human chorionic gonadotropin, i.p. (Choluron, Veterinaria), day 3, at 17:00, 48 h apart, in order to induce superovulation.

Females were caged with CBAxC57B1 males at the time of the HCG-injection (day 3).

Embryos at 6-8 cells were collected at day 5 after caging males and females and cultured either in vivo (group 1) or in vitro using a sequential medium culture (group 2). Only two female with a copulation plug were operated and used for this experiment.

Females were killed by cervical dislocation and laparotomy was performed to exteriorize the uterine horn and the tube in order to collect embryos.

Transfer of 6-8 cells embryos into the right or the left horn were performed at day 3 of two pseudopregnant females (recipients).

Group 1 embryos (in vivo culture) were loaded into a modified hollow fiber device according to the invention (semi permeable polyethersulfone (PES) hollow fibers, Source=Akzo Nobel FaserAG, Wuppertal, Germany) with an outer diameter=680 um and inner diameter=480 um of 0.5 cm length, attached to a 6.0 sterilized and non resorbable surgical thread by using a fine glass pipette under microscopic visualization.

A dorsal laparotomy was performed under ether anaesthesia according a standard procedure in order to exteriorize the right or the left horn and implant the intrauterine device with encapsulated zygotes into the lumen of right or left horn.

After fixing surgically the intrauterine device with encapsulated zygotes the horn was replaced in its anatomical position and hooks were used to close the skin.

After a period of 48 h transferred females were killed by cervical dislocation and laparotomy was performed to exteriorize the left or right horn containing the intrauterine device and to retrieve it.

Embryos were collected after cutting both distal part of the device and a capsule cavity flushing with culture medium.

Table 1 shows the results of two experiments comparing the in vivo and in vitro (as control) development of 6-8 cells embryos after 48 h culture.

In group 1, all encapsulated 6-8 cells embryos continued their development into the uterus similar to the control group. However, a delay was noted in development compared to the in vitro embryos culture.

This example shows for the first time that intrauterine device with encapsulated embryos may allow their natural incubation into the uterus with a possible development at least similar to the conventional in vitro culture.

From the available literature, IUD has ever been considered as hostile to fertility and always related to contraception. The presence of a foreign body in the uterine cavity is known to interfere with reproduction in all species. However, the affected steps of reproductive processes are far to be clear in literature. It appears that it may vary according to species. It is generally accepted that IMD induce a local inflammatory reaction in the endometrium. Whereas in mouse and rat this chronic infiltration of polymorphonuclear seems to be related to bacterial infection and to transforms the uterine endometrium in an hostile environment with embryo toxic secreted factors (Parr et al., 1967), 20 years after, Alvarez et al. (1988) showed in women that IUD may affect the fertilization before that the blastocyst enters the uterine cavity.

The above results demonstrating a mouse embryo development without degeneration are against the generally accepted scientific opinion that in animal models the uterus itself kills embryos by releasing several toxic factors.

The delay in development as shown in in vivo encapsulated embryos may be explained to the unoptimal size of pores or inner lumen diameter leading to a lower concentration of nutrients around it. Furthermore, the time itself which was sometimes several minutes in room temperature to implant the IUD with encapsulated embryos into the uterus before in vivo culture may explain thermic and gazous shockes with deleterious effect on preimplanted embryo.

Example 2

Intrauterine Erythropoietin Delivery

Intrauterine erythropoietin (Epo) delivery using a modified and invented encapsulated mouse Epo secreting mouse C2C12 cells decrease apopotosis in endometrium and increase blood hematocrit suggesting a direct effect of EPO on nearby endometrium tissue and systemic effect of Epo delivred from the uterus.

Erythropoietin is produced by the kidney in adults and the liver in fetuses. It is a key factor for regulating erythropoiesis by stimulating proliferation and differentiation of late erythroid precursor cells. It has been shown recently that the brain has a paracrine Epo/EpoR and that Epo may prevent neuronal apopotosis after cerebral ischemia (Sirén et al., 2001). Interestingly, Epo seems to be implicated in uterine angiogenesis.

Taking into account the above mentioned physiological effect of Epo, the evaluation of the effect of Epo on endometrium by delivering Epo from the uterus using the cell encapsulation device of the invention and the evaluation of the cell viability in this new implantation site for a device the uterine cavity by measuring the blood hematocrit have been made.

Mouse C2C12 myoblast cells were transfected with a plasmid containing the mouse Epo cDNA and a mutated dihydrofolate reductase (DHFR) gene for gene amplification upon administration of increasing doses of methotrexate.

Epo secreting cell lines were loaded into polyethersulfone microporus hollow fibers in order to be implanted into the uterine cavity. Characteristics of this novel invented cell encapsulation device are similar to the description in example 1.

A total of 14 devices were used implanted in a blinded fashion in the present experiment, group 1: mEpo-C2C12 (n=7) with Epo secretion and group 2: mEpo-C2C12 control cells (n=7) without Epo secretion.

At day 14, according to a standard accepted protocole for animal sacrifice, the uterus was removed and capsule retrieved in order to be pulsed for MEPO output. The uterus was fixed in 10% formol for immunohistochemistery and TUNEL assay to test apoptosis.

A significant increase blood hematocrite in group 1 with intrauterine Epo delivery (59.4+/−6.8) compared to group 2 without Epo delivery (45.7+/−2.9), $p \leq 0.005$ is noted after 14 days of intrauterine Epo delivery in 14 female mice (data not shown here).

It is noted that Epo, similar to its effect recently described in neuronal cells, decrease apoptosis in endometrium tissue.

The endometrium is thus a new target of Epo with a modulation of apoptosis.

Transfected cell line encapsulated in microporous hollow fiber are viable after 14 days of intrauterine incubation which has never been tested as implantation site for cell encapsulation device before.

Epo secreted by transfected cell line go across the microporous wall of the device and is resorbed through the endometrium and through the systemic circulation according to the significant increase of blood hematocrit intreated animals.

These results confirm that i) the uterus may be an excellent natural incubator confirming the results of example No1 for embryo development and ii) drug delivery may use in woman or female animals the uterine cavity as implantation site of a cell encapsulation system.

TABLE 1

| | t 48h | | | | | |
|---|---|---|---|---|---|---|
| | in vivo | | | in vitro | | |
| Experiments | 6–8 cells | morula | blastocysts | 6–8 cells | morula | blastocysts |
| No1 6–8 cells N = 30 | n = 20 | | | n = 10 | | |
| | 0 | 16 | 2* | 0 | 0 | 9‡ |
| No2 6–8 cells N = 22 | n = 12 | | | n = 10 | | |
| | 0 | 6 | 1 | 0 | 2 | 8 |

*early blastocysts, no retrieval after capsule flushing of 2 embryos
‡1 early blastocyst, 1 embryo losted

REFERENCES

Adaniya G K, Rawlins R G, Quigg J M, Roblero L, Miller I F, Zaneveld First pregnancies and livebirths from transfer of sodium alginate encapsulated embryos in a rodent model. L J Fertil Steril 1993 59:652-6.

Alvarez F, Brache V, Fernandez E, Guerrero B, Guiloff E, Hess R New insights on the mode of action of intrauterine contraceptive devices in women Fertil Steril 1988 49: 768-773

Barmat L I, Liu H C, Spandorfer S D, Xu K, Veeck L, Damario M A, Rosenwaks Z Human preembryo development on autologous endometrial coculture versus conventional medium. Fertil Steril 1998 70:1109-13

Boni R, Tosti E, Roviello S, Dale B. Intercellular communication in in vivo- and in vitro-produced bovine embryos Biol Reprod 1999 61: 1050-1055

Cosby N C, Dukelow W R Microencapsulation of single, multiple, and zona pellucida-free mouse preimplantation embryos in sodium alginate and their development in vitro. J Reprod Fertil 1990 90:19-24

Crosier A, Farin P, Dykstra M, Alexander J, Farin C. Ultrastructural morphometry of bovine compact morulae produced in vivo or in vitro Biol Reprod 2000 62: 1459-1465

Fassler R and Meyer M Consequences of lack of β1 integrin gene expression in mice. Genes and Development 1995 9:1876-1908

Fazleabas A, Donnelly K M, Srinivasan S, Fortman J D, Miller J B. Modulation of the baboon (papio anubis) uterine endometrium by chorionic gonadotrophin during the period of uterine receptivity. Proc Natl Acad Sci 1999 96:2543-8

Gardner D K, Lane M, Calderone I and Leeton J. Environnement of the preimplantation human embryo in vivo: metabolite analysis of oviduct and uterine fluids and metabolism of cumulus cells Fertil Steril 1996 65: 349-353

Gardner D K, Schoolcraft W B, Wagley L, Schlenker T, Stevens 3 and Hesla J. A prospective randomized trial of blastocyst culture and transfer in in vitro fertilization Hum Reprod 1998 13: 3434-3440

Gonzales D, Bavister B, Mese S. In utero and in vitro proteinase activity during the Mesocricetus auratus embryo zona escape time window Biol Reprod 2001 64: 222-230

Levran D, Farhi J, Nahum H, Royburt M, Glezerman M, Weissman A. Prospective evaluation of blastocyst stage transfer vs. zygote intrafallopian tube transfer in patients with repeated implantation failure Fertil Steril 2002 77: 971-977

Loi P, Ledda S, Gallus M, Filia F, Cappai P, Naitana S. Microencapsulation in Na-alginate and in vitro development of sheep blastomeres. Boll Soc Ital Biol Sper 1992 68:3114

Nebel R L, Vishwanath R, McMillan W H, Saacke R G Microencapsulation of bovine spermatozoa for use in artificial insemination: a review. Reprod Fertil Dev 1993:701-12

Parr E, Schlaedler R, Hirsch 3. The relationship of polymorphonuclear leukocytes to infertility in uteri containing foreign bodies IExp&Med 1967 126: 523-535

Robb L, Li R, Hartley L, Nandurkar H H, Koentgen K, Begley C G Infertility in female mice lacking the receptor for interleukin 11 is due to a defective uterine response to implantation. Nature Medicine 1998 4:303-308

Simon C, Mercader A, Garcia-Velasco J, Nikas G, Moreno C, Remohi J, Pellicer A Coculture of human embryos with autologous human endometrial epithelial cells in patients with implantation failure. J Clin Endocrinol Metab 1999 84:2638-46

Sirèn A-L, Fratelli M, Brines M et al. Erythropoietin prevents neuronal apoptosis after cerebral ischemia and metabolic stress Proc Natl Acad Sci 2001 98: 4044-4049

Shiotani M, Noda Y, Mori T. Embryo-dependent induction of uterine receptivity assessed by an in vitro model of implantation in mice. Biol Reprod 1993 49:794

Spandorfer S D, Barmat L I, Navarro J, Liu H C, Veeck L, Rosenwaks Z Importance of the biopsy date in autologous endometrial cocultures for patients with multiple implantation failures Fertil Steril 2002 77: 1209-1213

The invention claimed is:

1. A method of performing in utero preimplantatory incubation of an embryo or a zygote in assisted reproductive technology, comprising the steps of:
   providing one or more element(s) comprising an embryo, a zygote, male and/or female gametes, a fertilized oocyte, or any combination thereof,
   providing a retrievable intrauterine device comprising a capsule capable of being loaded with one or more elements comprising an embryo, a zygote, male and/or female gametes, a fertilized oocyte, or any combination thereof,
      wherein said capsule comprises a material that permits passage of proteins from a uterine cavity to said elements loaded in said capsule, when said device is placed in the uterine cavity,
   loading said capsule in said device with said element(s),
   placing said device within the uterine cavity of a mammal,
   retrieving and removing the device from the uterine cavity along with the encapsulated element(s) after incubation of said element(s) in contact with uterine fluids in said capsule,
   further retrieving an embryo or a zygote from said capsule.

2. The method of claim 1, wherein said element(s) comprise male and/or female gametes.

3. The method of claim 1, wherein said device is adapted for stable placement of the device in the uterus.

4. The method of claim 1, wherein said capsule comprises a polymeric material.

5. The method of claim 4, wherein said polymeric material comprises polyethersulfone, polyacrylates and acrylate copolymers, polyvinylidienes, polyurethanes, or a mixture thereof.

6. The method of claim 1, wherein said material that permits passage of proteins comprises a selectively permeable membrane with an adapted pore size.

7. The method of claim 6, wherein said membrane comprises a polyethersulfone.

8. The method of claim 1, wherein said material that permits passage of proteins has a molecular weight cutoff ranging from 50,000 to 1 million Daltons.

9. The method of claim 8, wherein the molecular weight cutoff is equal to or greater than 150,000 Daltons.

10. The method of claim 1, wherein material that permits passage of proteins has a molecular weight cutoff equal to or greater than 1 million Daltons.

11. The method of claim 1, wherein the device is loaded with an embryo or a zygote.

12. The method of claim 1, wherein said mammal is a human.

13. The method of claim 1, further comprising the step of: implanting the retrieved embryo or zygote into the uterine cavity of said mammal.

14. The method of claim 1, further comprising the step of: freezing the retrieved embryo or zygote for cryopreservation.

15. The method of claim 1, further comprising the step of: in-vitro culture of the embryo or zygote prior to implantation.

* * * * *

UNITED STATES PATENT AND TRADEMARK OFFICE
CERTIFICATE OF CORRECTION

PATENT NO. : 8,257,244 B2  
APPLICATION NO. : 10/485611  
DATED : September 4, 2012  
INVENTOR(S) : Pascal Mock Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1549 days.

Signed and Sealed this
Seventeenth Day of March, 2020

Andrei Iancu
*Director of the United States Patent and Trademark Office*